United States Patent [19]

Molaire et al.

[11] Patent Number: 5,176,977
[45] Date of Patent: Jan. 5, 1993

[54] NONPOLYMERIC AMORPHOUS DEVELOPER COMPOSITIONS AND DEVELOPING PROCESSES

[75] Inventors: Michel F. Molaire; Peter S. Alexandrovich, both of Rochester, N.Y.

[73] Assignee: Eastman Kodak Company, Rochester, N.Y.

[21] Appl. No.: 724,308

[22] Filed: Jul. 1, 1991

[51] Int. Cl.$^5$ ............................................. G03G 9/093
[52] U.S. Cl. ................... 430/106.6; 430/108; 430/109; 430/110; 430/904
[58] Field of Search ............... 430/106.6, 904, 108, 430/109, 110

[56] References Cited

U.S. PATENT DOCUMENTS

| | | | |
|---|---|---|---|
| 3,427,258 | 2/1969 | Trease | 252/500 |
| 3,577,345 | 5/1971 | Jacknow et al. | 252/62.1 |
| 3,609,082 | 9/1971 | Moriconi et al. | 252/62.1 |
| 3,884,825 | 5/1975 | Lindblad et al. | 252/62.1 |
| 3,980,575 | 1/1978 | De Roo et al. | 252/62.1 P |
| 4,073,739 | 2/1978 | Peters | 252/62.1 P |
| 4,099,968 | 7/1978 | Scouten et al. | 96/15 D |
| 4,222,982 | 9/1980 | Beatty et al. | 264/143 |
| 4,233,388 | 11/1980 | Bergen et al. | 430/137 |
| 4,299,899 | 11/1981 | Azar et al. | 430/108 |
| 4,499,165 | 2/1985 | Molaire | 430/17 |
| 4,507,376 | 3/1985 | Makita et al. | 430/109 |
| 4,508,806 | 4/1985 | Oseto et al. | 430/109 |
| 4,626,361 | 12/1986 | Molaire | 252/1 |
| 4,778,742 | 10/1988 | Ong et al. | 430/106 |
| 4,812,377 | 3/1989 | Wilson et al. | 430/109 |
| 4,833,057 | 5/1989 | Misawa et al. | 430/109 |
| 4,859,558 | 8/1989 | Matsumura et al. | 430/110 |

*Primary Examiner*—Marion E. McCamish
*Assistant Examiner*—Rosemary Ashton
*Attorney, Agent, or Firm*—W. T. French; A. P. Lorenzo; B. D. Wiese

[57] ABSTRACT

Toner and developer compositions incorporating nonpolymeric, homogeneous, amorphous mixtures of compounds as the binder are described. The mixtures comprise at least two nonpolymeric, thermoplastic organic compounds each having at least two linking components joining one multivalent organic nucleus with at least two organic appended groups wherein either the multivalent organic nucleus or at least one of the appended groups in an aromatic group. The mixtures have glass transition temperatures of 50° to 120° C. Methods for developing electrostatic images with the developer compositions are also described.

20 Claims, No Drawings

5,176,977

NONPOLYMERIC AMORPHOUS DEVELOPER COMPOSITIONS AND DEVELOPING PROCESSES

FIELD OF THE INVENTION

This invention relates to electrographic toner and developer compositions and developing processes and, in particular, to the use of certain fusible, nonpolymeric amorphous mixtures of compounds as the binder in such toner and developer compositions.

BACKGROUND OF THE INVENTION

Electrophotographic imaging and developing processes have been extensively described in the patent literature. As described in U.S. Pat. No. 2,297,691 to Carlson, the basic process involves placing a uniform electrostatic charge on a photoconductive insulating layer, exposing the layer to a light and shadow image to dissipate the charge on the areas exposed to the light and developing the resulting latent electrostatic image by depositing on the image a finely divided electroscopic material known as "toner". The toner may normally be attracted to those areas of the layer which retain a charge, thereby forming a toner image corresponding to the latent electrostatic image. This powder image may then be transferred to a support surface such as paper. The transferred image may subsequently be permanently affixed to the support surface as by heat.

Various methods for applying the toner particles to the latent electrostatic image are known. In the "cascade" method, as described in U.S. Pat. No. 2,618,552 to Wise, toner particles charged triboelectically to the desired polarity are conveyed to and rolled or cascaded across the electrostatic latent-image-bearing surface. The toner particles are electrostatically deposited on and secured to the charged portion of the latent image. Most of those toner particles accidentally deposited in the background are removed by the rolling carrier due, apparently, to a greater electrostatic attraction between the toner and the rolling carrier than between the toner and the discharged background.

In another method, the "magnetic brush" method, disclosed, for example, in U.S. Pat. No. 2,874,063, developer material containing toner and magnetic carrier particles are carried by a magnet. The magnet's field causes the magnetic carrier to align in a brush-like configuration. When the "magnetic brush" is engaged with the electrostatic latent-image-bearing surface, the toner particles are drawn from the brush to the latent image by electrostatic attraction.

Other patents describing the electrophotographic process, and in particular various toner compositions, include U.S. Pat. Nos. 3,609,082 to Moriconi et al., 4,508,806 to Oseto et al., 4,859,558 to Matsumura et al. and 3,893,935 to Jadwin et al. As these patents indicate, typically the toner composition comprises a resinous binder suitably colored or darkened, for contrast purposes, with a colorant like dyestuffs or pigments such as carbon black. Toner particles may be used as single component "developers" or alternatively, as described in U.S. Pat. No. 3,893,935 to Jadwin et al., they may be combined with a carrier vehicle that can either be a magnetic material such as iron filings, powdered iron or iron oxide, or a triboelectrically chargeable non-magnetic substance like glass beads or crystals of inorganic salts such as sodium or potassium fluoride.

In addition to the resinous binder and colorant components of the toner composition, a variety of additives for modifying the surface properties of particulate toner particles have been described. For example, various charge control agents may be used to modify the surface properties of the toner powder so that a uniform, stable high net electrical charge may be imparted to the toner powder by the particulate carrier vehicle. Examples of charge control agents include the mono- or difunctional organic and nigrosine salts disclosed in U.S. Pat. No. 3,647,696 to Olson, the long chain quarternary ammonium surfacants disclosed in British Patent No. 1,174,573 and the quarternary ammonium salts described in U.S. Pat. No. 3,893,935 to Jadwin et al.

In addition to charge control, two other important properties of a toner composition are low temperature fusibility and pulverizability. By pulverizability we mean the relative ease with which the toner composition may be ground to very small particles. Relatively low temperature fusibility is important because the toner must be readily fusible without excessive energy cost and without scorching or charring of the paper support. Unfortunately, conventional toner materials that are easily fused by heating sometimes tend to cake or agglomerate during handling and storage and tend to form tacky images. This agglomeration or "blocking" phenomenon, as it is known, is described in, for example, U.S. Pat. Nos. 4,508,806 to Azar et al. and 3,980,575 to De Roo et al. Agglomeration or blocking is directly at odds with the high resolution of electrophotographic images which depends in part on the presence of small discrete particles of toner to define only the latent image area without edge overlap, smear, etc.

For this reason, liquid toners have been favored for electrostatographic applications directed to optimum image resolution because the small size of the toner particles allows finer edge discrimination. Unfortunately, stable multiphase dispersions of solid particles in a liquid medium are difficult to prepare, to store, and to use. Preparation of such toners involves delicate balancing of surfactants which provide dispersion stability, with charge control agents which control image discrimination of the particle for the latent image site. The dispersions employ large quantities of flammable organic solvents as the dispersion media, and these solvents must be removed from toned prints. Further, being flammable, malodorous organic solvents, measures must be taken to prevent environmental contamination during use.

One attempt to solve the apparent incompatibility of these two desirable properties, i.e., low temperature fusibility and good pulverizability is described in U.S. Pat. No. 4,233,388 to Bergen et al. As described therein, one disadvantage of conventional easily fusible toner compositions, which typically employ low molecular weight resins as the binder, is that they tend to form thick films on reusable photoconductor surfaces. These films tend to cause image degradation and contribute to machine maintenance down-time. Similarly, low molecular weight resin toner compositions tend to "impact" or become welded on the surface of carrier particles, thus adversely affecting the triboelectric properties of developer mixtures. Furthermore, some low molecular weight resins are difficult or even impossible to pulverize in a conventional grinding apparatus.

In U.S. Pat. No. 4,233,388, Bergen et al. proposed as a solution to these problems a method for making toner particles in which low molecular weight polymers are first melted and blended with other toner components such as colorants. Films or fibers of the colored polymer materials are then preferably subjected to a molecular orientation step to improve their mechanical properties, and are finally embossed or cut to the desired particle size by passing the films or fibers through embossing or cutting rollers.

By this method, low molecular weight polymers are made as resistant to film formation and impaction as conventional resin polymers, and toner particles of any size within the range from about 1 to about 30 microns may be obtained. This complex process, however, results in additional steps in the preparation of toner compositions, and therefore, additional expense.

There is, therefore, a need for solid electrographic toner compositions which can be readily ground to unusually fine particle size (i.e., less than about 5μ) to improve the resolution of electrographic images toned with said solid toner developers, while being fusible at relatively low temperatures.

SUMMARY OF THE INVENTION

In accordance with the present invention, a powdered toner composition of finely divided thermally fusible particles is provided which achieves both low temperature fusibility and good pulverizability. These two desirable properties are unexpectedly achieved by incorporating as the binder in electrostatographic toner and developer compositions a homogenous, amorphous mixture of at least two nonpolymeric thermoplastic organic compounds, each compound in the mixture having at least two linking components joining one multivalent organic nucleus with at least two organic appended groups. Either the multivalent organic nucleus or at least one of the organic appended groups is an aromatic group. The particles of the toner composition comprise a homogenous blend of a major amount of the amorphous mixture and a colorant. The developer compositions comprise toner composition particles and magnetic carrier particles. The amorphous mixture has a glass transition temperature ranging from about 50° to about 120° C.

DETAILED DESCRIPTION OF THE INVENTION

The powdered toner and developer compositions of the present invention employ as the binder certain mixtures of compounds disclosed in U.S. Pat. No. 4,499,165 to Molaire, although that reference discloses the use of the mixtures in optical recording layers and elements. No suggestion is made of the amenability of the mixtures to pulverization into very small particles for use in toner and developer compositions.

Specifically, the nonpolymeric, amorphous mixtures of compounds useful as the binders of the toner and developer compositions of this invention are homogeneous mixtures of at least two nonpolymeric, thermoplastic compounds, each compound in the mixture independently conforming to the structure:

$(R^1Y^1)_p[(Z^1Y^2)_mR^2Y^3]_nZ^2Y^4R^3$ wherein
m is zero or one;
n is the number of recurring units in the compound, and is zero up to, but not including, an integer at which said compound starts to become a polymer;
p is an integer of from one to eight;
each $R^1$ and $R^3$ is independently a monovalent aliphatic or cycloaliphatic hydrocarbon group having 1 to 20 carbon atoms, an aromatic group or a multicyclic aromatic nucleus;
$R^2$, $Z^1$ and $Z^2$ each independently represent multivalent aliphatic or cycloaliphatic hydrocarbon groups having 1 to 20 carbon atoms or an aromatic group; $Y^1$, $Y^2$, $Y^3$, $Y^4$ each independently represents one or more linking groups such as esters (—COO—), amides (—CONH—), urethanes (—NHCOO—), imides

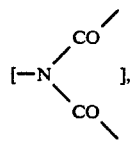

nitrilomethyleneoxys

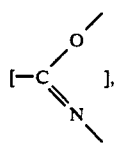

nitrilomethyleneiminos

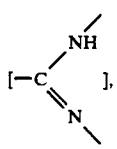

nitrilomethylenethios

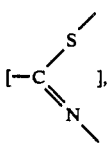

1,3,4-triazol-2,5-ylenes

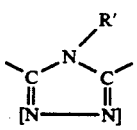

wherein R' represents alkyl of 1–6 carbon atoms, hydroxyl, amino or aryl such as phenyl and 1,3,4-oxadiazol-2,5-ylenes

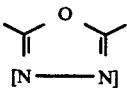

provided that at least one of $R^1$, $Z^1$, $R^2$, $R^3$ and $Z^2$ is an aromatic group and the glass transition temperature (Tg) of the mixture ranges from 50° to 120° C.

In the structural formula, the expression "$[(Z^1Y^2)_m\text{-}R^2Y^3]_n$" describes nonpolymeric compounds which are oligomers. Oligomers are usually formed when either $Z^1$ or $R^2$ are at least bivalent. The $(Z^1Y^2)_m$ moiety describes oligomers in which $Z^1$ repeats itself such as when $Z^1$ is derived from p-hydroxybenzoic acid. When n is one or more, p in the structural formula is preferably one to avoid significant crosslinking of the compound due to the multivalent nature of $Z^1$. However, some crosslinking can be tolerated in binder-mixtures for toner and developer compositions.

In general, the Tg of the binder is high enough to provide suitable storage stability, yet low enough to allow low temperature fusing and extended fusing latitude. In one preferred embodiment of the invention, the Tg of the mixture ranges from 55° to 80° C.

A "multicyclic aromatic nucleus" is a nucleus comprising at least two cyclic groups at least one of which is aromatic, including aromatic heterocyclic ring groups. The cyclic group may be substituted with substituents such as aliphatic hydrocarbons, including cycloaliphatic hydrocarbons, other aromatic ring groups such as aryl, and heterocyclic ring groups such as substituted or fused thiazole, oxazole, imide, pyrazole, triazole, oxadiazole, pyridine, pyrimidine, pyrazine, triazine, tetrazine and quinoline groups. The substituents are fused or non-fused and mono or polycyclic. Examples of multicyclic aromatic nuclei include 9,9-bis(4-hydroxy-3,5-dichlorophenyl)fluorene, 4,4'-hexahydro-4,7-methanoindan-5-ylidenebis(2,6-dichlorophenol); 9,9-bis(4-hydroxy-3,5-dibromophenyl)fluorene, 4,4'-hexahydro-4,7-methanoindan-5-ylidenebis(2,6-dibromophenol); 3',3'',5',5''-tetrabromophenolphthalein, 9,9-bis(4-aminophenyl)fluorene, phenylindandiols; 1,1'-spirobiindandiols, 1,1'-spirobiindandiamines, 2,2'-spirobichromans; 7,7-dimethyl-7H-dibenzo[c,h]xanthenediol; xanthylium salt diols; 9,9-dimethylxanthene-3,6-bis(oxyacetic acids); 4,4'(3-phenyl-1-indanylidene)-diphenol and other bisphenols; 3',3''-dibromo-5',5''-dinitro-2',2''-oxaphenolphthalein; 9-phenyl-3-oxo-2,6,7-trihydroxyxanthene; and the like.

"Aliphatic hydrocarbon group" for $R^1$, $R^2$, $R^3$, $Z^1$ and $Z^2$ refers to monovalent or divalent, alkanes, alkenes, alkadienes and alkynes having from 1 to 20 carbon atoms. The groups are straight or branched chain and include carbohydrate, carboxylic acid, alcohol, ether, aldehyde and ketone functions. "Cycloaliphatic" refers to cyclic aliphatic hydrocarbon groups. The groups may be substituted with halogen, alkoxy, amide, nitro, ester and aromatic groups.

Although the compounds in the mixture are nonpolymeric, compounds which are oligomers are included in the mixtures. The nonpolymeric compounds in the mixtures of the invention are distinguished from polymers according to the following relationship.

The qualitative relationship between the log viscosity (log $\eta$) to the log molecular weight (log MW) of a compound is linear. At a critical molecular weight (MWc) or critical viscosity ($\eta_c$) the slope of a curve illustrating that relationship changes sharply, for example, from about 1 to about 3.4. Above MWc or $\eta_c$ the compound is polymeric. Below MWc or $\eta_c$, the compound is a monomer or an oligomer and is within the scope of this invention. MWc and $\eta_c$ is not fixed, and varies with the structure of the particular compound. See *Fundamental Principles of Polymeric Materials for Practicing Engineers* by Stephen L. Rosen, Barnes and Noble, Inc., N.Y., N.Y., (1971), pages 176 and 177. In general, it is believed that compounds having a molecular weight up to about 5000 or up to about 10 recurring units are useful in the mixtures of this invention, although it is expected that compounds having a molecular weight greater than 5000 or more than 10 recurring units will in some circumstances be operable.

In another embodiment of the invention, the nonpolymeric, amorphous mixtures of compounds useful as the binders of the toner compositions of this invention are homogenous mixtures of at least two nonpolymeric, thermoplastic compounds, each compound in the mixture independently conforming to the structure:

$$Z(Y\text{-}R)_n$$

wherein n is two to eight;

Z is a straight or branched chain, substituted or unsubstituted aliphatic group optionally having hetero atom groups in or appended thereto, or a substituted or unsubstituted homo- or heterocyclic, mono- or polycyclic group;

each R group independently from the other R groups, is a straight or branched chain, substituted or unsubstituted aliphatic group optionally having hetero atom groups in or appended thereto, or a substituted or unsubstituted homo- or heterocyclic, mono- or polycyclic group;

each Y, which may be the same or different from the other Y groups, is an ester, amide, imide or urethane linkage joining the nucleus Z to an appended group R;

provided that at least one Z or R group is an aromatic group, the mixture comprises at least two different R groups and the Tg of the mixture ranges from 50° to 120° C.

For the nucleus Z, "aliphatic group" refers to divalent or multivalent alkanes, alkenes, alkadienes and alkynes having from 1 to 20 carbons. The groups are straight or branched chain and include carbohydrate, carboxylic acid, alcohol, ether, aldehyde and ketone functions. The groups may be substituted with halogen, alkoxy, amide, nitro, ester and aromatic groups. Monovalent versions of the same types of aliphatic groups are suitable R groups.

The term "amorphous" means that the mixture is noncrystalline. That is, the mixture has no molecular lattice structure.

Exemplary aliphatic groups include methyl, ethyl, propyl, isopropyl, butyl, hexyl, 2-ethylhexyl, methoxyethyl, ethoxycarbonylpropyl, 3-oxobutyl, 3-thiapentyl, furfuryl, 2-thiazolylmethyl, cyclohexylmethyl, benzyl, phenethyl, phenoxyethyl, vinyl (—CH=CH—), 2-methylvinyl, allyl, allylidene, butadienyl, butenylidene, propargyl, etc.

"Aromatic" and "aromatic heterocyclic" group refer to organic groups which undergo the same type of substitution reaction as benzene. In benzene, substitution reactions are preferred over addition reactions. Such groups preferably have from 6 to about 40 nuclear atoms and are mono- and polycyclic.

Exemplary aromatic groups include quinolinyl, pyrimidinyl, pyridyl, phenyl, tolyl, xylyl, naphthyl, anthryl, triptycenyl, p-chlorophenyl, p-nitrophenyl, p-bromophenyl, 2,4-dichlorophenyl, 2-chlorophenyl, 3,5-dinitrophenyl, p-(tetrabromophthalimido)phenyl, p-

(tetrachlorophthalimido)phenyl, p-tetraphenylphthalimido)phenyl, p-naphthalimidophenyl, p-(4-nitrophthalimido)phenyl, p-phthalimidophenyl, 1-hydroxy-2-naphthyl, 3,5-dibromo-4-(4-bromobenzoyloxy)phenyl, 3,5-dibromo-4-(3,5-dinitrobenzoyloxy)phenyl, 3,5-dibromo-4(1-naphthoyloxy)phenyl, thiazolyl, oxazolyl, imidazolyl, pyrazolyl, triazolyl, oxadiazolyl, pryazinyl, etc. and their corresponding multivalent and fused ring configurations.

The mixtures of the present invention are made by the method disclosed in U.S. Pat. No. 4,499,165 to Molaire, which is incorporated herein by reference. Representative starting materials having a multicyclic aromatic nucleus and at least two functional (reactive) groups are selected from the following materials:

A. The phenylindan diols of J. C. Wilson, Research Disclosure 11833, February 1974, and J. C. Wilson, U.S. Pat. Nos. 3,803,096, 3,859,364 and 3,886,124 and the phenylindan diamines of J. C. Wilson, U.S. Pat. Nos. 3,897,253 and 3,915,939 having the structures:

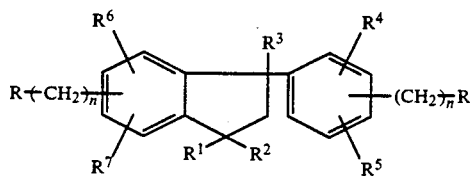

and

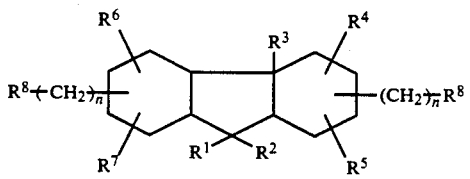

wherein $R^1$ and $R^3$ are independently selected from the group consisting of hydrogen and alkyl radicals of from 1 to 6 carbon atoms; $R^2$ is an alkyl radical of from 1 to 6 carbon atoms; $R^4$, $R^5$, $R^6$, and $R^7$ are independently selected from the group consisting of hydrogen, aryl radicals, halogen atoms, nitro radicals, cyano radicals, amino radicals, and alkoxy radicals; R is hydroxy or amino; and n is 0 or 1.

B. The 1,1'-spirobiindan diols and diamines of F. L. Hamb and J. C. Wilson, U.S. Pat. No. 3,725,070; and the 1-1'-spirobiindan (dicarboxylic acids) of Research Disclosure 9830, June, 1972 (anonymous), of the structure:

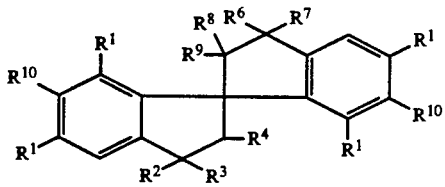

wherein each $R^1$ independently is selected from the group consisting of hydrogen atoms, or alkyl radicals having 1 to 12 carbon atoms; $R^2$, $R^3$, $R^4$, $R^5$, $R^6$, $R^7$, $R^8$, and $R^9$ are independently selected from the group consisting of hydrogen atoms and alkyl radicals of from 1 to 5 carbon atoms; $R^{10}$ is —OH, —NH$_2$, or —OCH$_2$COOH.

C. The 1,1'-spirobiindan-5,5'-diamines of J. C. Wilson, Research Disclosure 13117, March, 1975, with the structure:

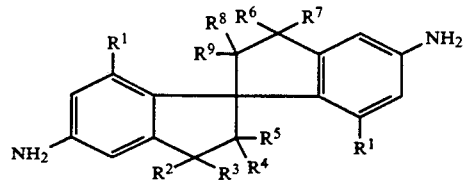

wherein each $R^1$ is independently selected from hydrogen atoms and alkyl radicals of 1 to 12 carbon atoms; and $R^2$, $R^3$, $R^4$, $R^5$, $R^6$, $R^7$, $R^8$, and $R^9$ are independently selected from the group consisting of hydrogen atoms and alkyl radicals of from 1 to 5 carbon atoms.

D. The 2,2'-spirobichromans of F. L. Hamb and J. C. Wilson, U.S. Pat. No. 3,859,097 of the structure:

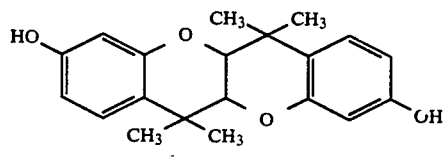

E. The 7,7-dimethyl-7H-dibenzo[c,h]xanthene diols of F. L. Hamb and J. C. Wilson, U.S. Pat. Nos. 3,859,254 and 3,902,904 of the structure:

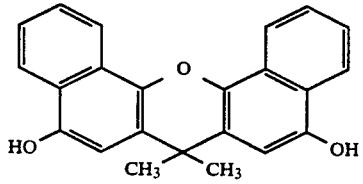

F. The 9,9-dimethylxanthene-3,6-bis(oxyacetic acids) of Research Disclosure 9830, June, 1972 (Anonymous) with the structure:

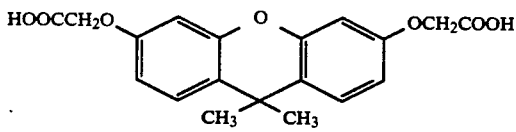

G. The xanthylium salts of J. C. Wilson, U.S. Pat. No. 3,856,751, with the structure:

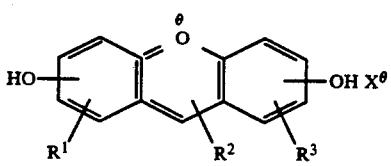

wherein $R^1$, $R^2$ and $R^3$ are hydrogen, alkyl, aryl, halogen, alkoxy, or cyano; and $X^\ominus$ is an acid anion.

H. The 4,4-(3-phenyl-1-indanylidene)diphenols of J. C. Wilson, Research Disclosure 13101, March, 1975, with the structure:

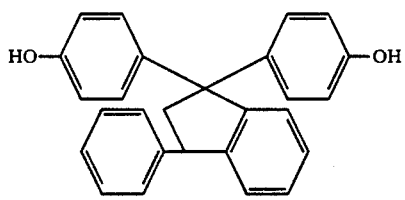

I. The 4,4-(hexahydro-4,7-methanoindan-5-ylidene)-diphenols of M. A. Sandhu, Research Disclosure 13568, July, 1975, with the structure:

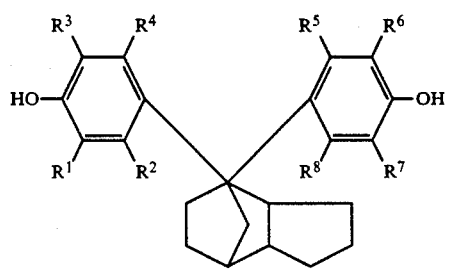

wherein $R^1$, $R^2$, $R^3$, $R^4$, $R^5$, $R^6$, $R^7$, and $R^8$ are independently hydrogen, halogen, cyano, alkyl of 1 to 8 carbon atoms, or alkoxy of 1 to 8 carbon atoms.

J. The bisphenols of T. L. Conklin and F. L. Hamb, Research Disclosure 12012, April, 1974, and the halogenated bisphenols of M. A. Sandhu, Research Disclosure 13569, July, 1975, with the structure:

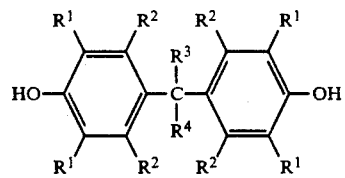

wherein each $R^1$ is hydrogen, halogen, preferably chloro or bromo, alkyl of 1 to 8 carbon atoms, or alkoxy of 1 to 8 carbons; each $R^2$ is hydrogen, alkyl of 1 to 8 carbon atoms or alkoxy of 1 to 8 carbon atoms; and $R^3$ and $R^4$ are alkyl of about 1 to 6 carbon atoms.

K. The sulfonyldibenzoic acids of M. A. Sandhu, Research Disclosure 14016, December, 1975, with the structure:

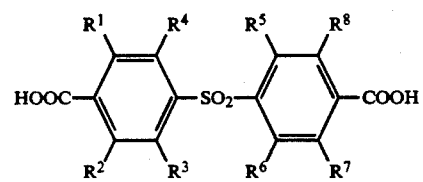

wherein each of $R^1$ through $R^8$ is independently from hydrogen, halogen, preferably chloro or bromo, and alkyl of about 1 to 4 carbon atoms.

L. The polycyclic norbornanes of Research Disclosure 9207, December, 1971 (Anonymous), with the structure:

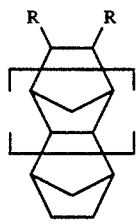

wherein n is 0 to 3 and R is —COOH or —CH$_2$OH.

M. The 1,2,3,4-tetrahydronaphthalenes of M. A. Sandhu, Research Disclosure 13570, July, 1975, with the structure:

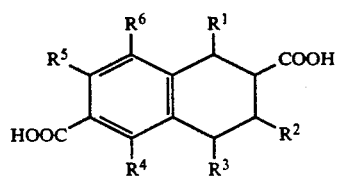

wherein each of $R^1$ through $R^6$ is independently selected from hydrogen, halogen or lower alkyl at 1 to 4 atoms.

Other useful polyfunctional compounds include commercially available bisphenols such as tetrabromophenolphthalein, tetrachlorophenolphthalein, tetrabromophenol blue, Eosin B, tetrabromocresol blue, hematoxylin, 4',5'-diodofluorescein, the polyhydroxy aromatic condensation product of pyrogallol and acetone, quercetin and derivatives thereof, the 9,9-bis(4-amino-3-benzoylphenyl)fluorene, 9,9-bis(4-aminophenyl)-10-anthrone and derivatives thereof reported in Macromolecules 14, p. 486–493 (1981), and other multifunctional molecules susceptible to quantitative condensation reaction to yield mixed esters, or mixed amides, or mixed imides, or mixed urethanes, or any other mixtures of organic materials that are noncrystallizable, and have glass-transition temperatures well above room temperature, i.e., above 50° C., preferably above 55° C.

Examples of monofunctional compounds that can be incorporated into the "nonpolymeric" amorphous glasses of this invention include:

1. Substituted benzene functionalized compounds of the structure:

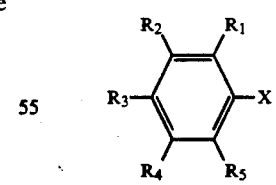

wherein $R_1$, $R_2$, $R_3$, $R_4$ and $R_5$ are independently selected from the group consisting of hydrogen, aryl radicals, halogen atoms, nitro radicals, cyano radicals, amino radicals and alkoxy radicals, and X is selected from the group consisting of primary or secondary amino radicals, hydroxy radicals, acid radicals, isocyanate radicals, etc.

2. Substituted phthalic anhydride compounds of the structure:

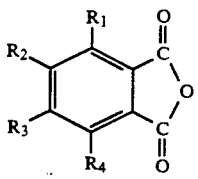

wherein $R_1$, $R_2$, $R_3$, $R_4$ are independently selected from the group consisting of hydrogen, aryl radicals, halogen atoms, nitro radicals, cyano radicals, and alkoxy radicals.

3. Aliphatic acids, alcohols, isocyanates, amines, and derivatives thereof. Aliphatic monofunctional compounds are particularly useful in controlling the glass transition temperature of the mixture within the range useful for toner applications.

4. Compounds having unsaturated polymerizable or crosslinkable groups such as acrylic acid, methacrylic acid and derivatives thereof, allyl alcohol, etc.

5. Any other monofunctional compounds susceptible to quantitative reactions amenable to the "nonpolymeric" amorphous glasses of this invention.

Some commercially available nonpolymeric glasses useful in the practice of this invention are the various derivatives of rosin available under many trade names. Examples are given in Table I.

TABLE I

| Commercially Available Nonpolymeric Glasses | | |
|---|---|---|
| Tradename* | Type | Softening Point, °C. |
| "Ester Gum 8 BG" | glycerol ester of wood rosin | 90 |
| "Pexalyn/A500" | glycerol ester of wood rosin | 86 |

The above products are available from Hercules, Inc., Hercules Plaza, Wilmington, DE 19894. For these amorphous materials, the softening point approximates the glass transition temperature. In any case, the glass transition temperatures for these materials are within the 50° to 120° C. range.

A variety of colorant materials selected from dyestuffs or pigments may be employed in the toner materials of the present invention. Such materials serve to color the toner and/or render it more visible. Of course, suitable toner materials having the appropriate charging characteristics can be prepared without the use of a colorant material where it is desired to have a developed image of low optical opacity. In those instances where it is desired to utilize a colorant, the colorants used, can, in principle, be selected from virtually any of the compounds mentioned in the *Colour Index* Volumes 1 and 2, Second Edition.

Included among the vast number of useful colorants would be such materials as Hansa Yellow G (C.I. 11680), Nigrosine Spirit soluble (C.I. 50415), Chromogen Black ET00 (C.I. 45170), Solvent Black 3 (C.I. 26150), Fuchsine N (C.I. 42510), C.I. Basic Blue 9(C.I. 52015), etc. Carbon black also provides a useful colorant. The amount of colorant added may vary over a wide range, for example, from about 1 to about 20 percent of the weight of the binder. Particularly good results are obtained when the amount is from about 2 to about 10 percent. In certain instances, it may be desirable to omit the colorant, in which case the lower limit of concentration would be zero.

The amount of charge control agent which may be incorporated in the powdered toner compositions of this invention is preferably in the range from 0.2 to 5 weight percent of the toner composition.

The toners of this invention can be mixed with carrier particles to form dry developer compositions. The carrier particles which can be used with the present toners to form new developer compositions can be selected from a variety of materials. Suitable carrier vehicles useful in the invention include various nonmagnetic particles such as glass beads, crystals of inorganic salts such as sodium or potassium chloride, hard resin particles, metal particles, etc. In addition, magnetic carrier particles can be used in accordance with the invention. Suitable magnetic carrier particles are particles of ferromagnetic materials such as iron, cobalt, nickel, and alloys and mixtures thereof. Other useful materials which exhibit a net magnetic moment are the ferrimagnetic materials, including the ferrites as described in U.S. Pat. Nos. 3,795,618 to Kasper and 4,546,060 to Miskinis et al., which are incorporated herein by reference. Particularly preferred are strontium and barium ferrites. Other useful magnetic carriers are ferromagnetic particles overcoated with a thin layer of various film-forming resins, for example, the alkali-soluble carboxylated polymers described in U.S. Pat. No. 3,547,822 to Miller; U.S. Pat. No. 3,632,512 to Miller; U.S. Pat. No. 3,795,617 to McCabe, entitled "Electrographic Carrier Vehicle and Developer Composition—Case B"; Kasper et al., U.S. Ser. No. 236,584, now abandoned, filed Mar. 21, 1972, entitled "Electrographic Carrier Vehicle and Developer Composition—Case C", and U.S. Pat. No. 3,795,618 to Kasper entitled, "Electrographic Carrier Vehicle and Developer Composition—Case D". Further useful resin coated magnetic carrier-particles include carrier particles coated with various fluorocarbons such as polytetrafluoroethylene, polyvinylidene fluoride, and mixtures thereof including copolymers of vinylidene fluoride and tetrafluoroethylene.

A typical dry developer composition containing the above-described toner and a carrier vehicle generally comprises from about 1 to 20 percent by weight of particulate toner particles and from about 80 to about 99 percent by weight carrier particles. Typically, the carrier particles are larger than the toner particles. Conventional carrier particles have a particle size on the order of from about 2 to about 200 microns.

The present invention provides nonpolymeric amorphous organic glass toner compositions that are easily grindable to exceptionally fine particles. The nonpolymeric amorphous organic glass toner compositions of this invention are particularly useful in any imaging process wherein a visible image is formed by depositing toner in an imagewise fashion on any substrate and the visible image is made permanent by fixing the toner image to the substrate by heated-roller fusing or by any other fusing techniques known in the art. Such developable charge patterns can be prepared by a number of means and can be carried, for example, on a light sensitive photoconductive element or a non-light sensitive dielectric surfaced element such as a receiver sheet. Processes in which the toner and developer compositions of the present invention are useful include electrophotography, dielectric recording, magnetic image formation, and the like.

Examples 1 through 3 illustrate the preparation of the nonpolymeric amorphous mixtures of this invention.

Glass transition temperatures were determined by differential scanning calorimetry analysis at a heating rate of 10°/min. or 20°/min. as specified. Example 4 illustrates the preparation and evaluation of the toner and developer compositions of this invention.

EXAMPLE 1

Preparation of an Amorphous Glass Mixture from 4,4'-Isopropylidenebis-(2,6-dibromophenol), Acryloyl Chloride (40 mole %), Methacryloyl Chloride (40 mole %) and Benzoyl Chloride (20 mole %)

4,4'-Isopropylidenebis(2,6-dibromophenol) 178.4 g (0.328 mole), acryloyl chloride 23.74 g (0.262 mole), methacryloyl chloride 274 g (0.262 mole) benzoyl chloride 18.43 g (0.131 mole), all are dissolved in approximately 1 liter of 1,2-dichloroethane, in a three-neck, round-bottomed flask. A condenser fitted with a drying tube and a positive-pressure nitrogen system is used to keep moisture out of the reactor vessel.

Triethylamine 70.5 g (0.697 mole) dissolved in 100 ml of 1,2-dichloroethane is added dropwise to the stirred solution in the reaction flask. After complete addition of the triethylamine, the reaction is allowed to continue for three additional hours at which time the precipitated salt is filtered off. The solution is subjected to the following extraction sequence:
  a) two dilute sodium hydroxide solution washes (2% cold)
  b) two dilute hydrochloric acid solution washes (4%)
  c) two distilled water washes The dichloroethane solution is then dried over magnesium sulfate and the solvent removed by evaporation at 90° C. under vacuum. To the dried amorphous glass 100 ml of tetrahydrofuran (THF) is added. The solution obtained is stirred into 4 liters of distilled water in a Waring blender to precipitate the product. The product is collected by filtration as very fine particles and dried. The Tg was 55° C. (20°/min., differential scanning calorimetry).

This is a modified Schotten-Bauman procedure, designed to increase the probability of mixed ester formation. The conventional Schotten-Bauman procedure involves dissolving the acid acceptor and the bisphenol in the flask and adding the acid chloride to the mixture. By having the bisphenol and the acid chlorides present in the complete stoichiometry and adding the acid acceptor to the mixture, we increase the probability of unsymmetrical ester formation and at the same time decrease the formation of symmetrical esters. This allows us to control the "noncrystallizability" of the finished mixture.

EXAMPLE 2

Preparation of an Amorphous Glass Mixture from 3',3'',5',5''-Tetrabromophenolphthalein (45 mole %), 4,4'-Isopropylidenebis(2,6-dibromophenol) (55 mole %), Acryloyl Chloride (50 mole %) and Methacryloyl Chloride (50 mole %)

This "nonpolymeric" amorphous glass was prepared using the procedure of Example 1 from 41.28 g (0.075 g mole) of 4,4'-isopropylidenebis-(2,6-dibromophenol), 43.09 g (0.0621 mole) of 3',3'',5',5''-tetrabromophenolphthalein, 12.50 g (0.138 mole) of acryloyl chloride 14.43 g (0.138 mole) of methacryloyl chloride and 30 g (0.297 mole) of triethylamine. The mixture Tg was 59° C. (20°/min., differential scanning calorimetry).

EXAMPLE 3

Preparation of a Nonpolymeric Amorphous Glass Mixture from 3',3'',5',5''-Tetrabromophenolphthalein (25 mole %), 4,4'-Isopropylidenebis (2,6-dibromophenol (75 mole %), Acryloyl Chloride (40 mole %), Methacryloyl Chloride (40 mole %), Benzoyl Chloride (10 mole %) and Phenylacetyl Chloride (10 mole %)

This nonpolymeric amorphous glass mixture was prepared using the procedure of Example 1 from 56.30 g (0.1035 mole) of 4,4'-isopropylidenebis (2,6-dibromophenol), 23.94 (0.0345 mole) of 3',3'',5',5''-tetrabromophenolphthlein, 10 g (0.1104 mole) of acryloyl chloride, 11.54 g (0.1104 mole) of methacryloyl chloride, 3.88 g (0.0276 mole) of benzoyl chloride, 4.27 g (0.0276 mole) of phenylacetyl chloride and 30 g (0.297 mole) of triethylamine. The mixture Tg was 64° C. (20°/min., differential scanning calorimetry).

Table II presents mixtures prepared by this method.

TABLE II

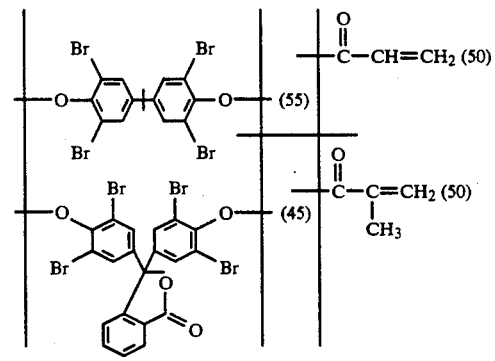

Tg = 59° C.

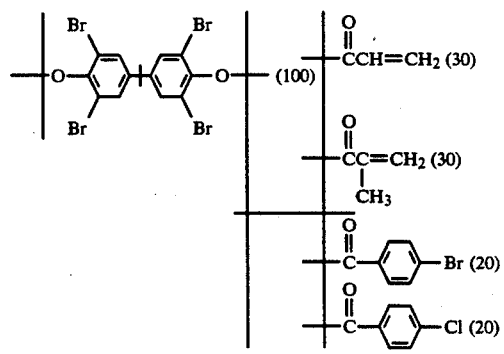

Tg = 57° C.

TABLE II-continued
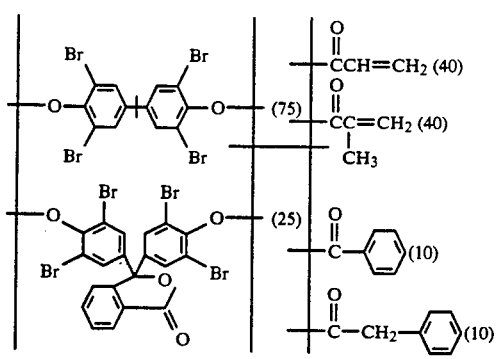
Tg = 64° C.
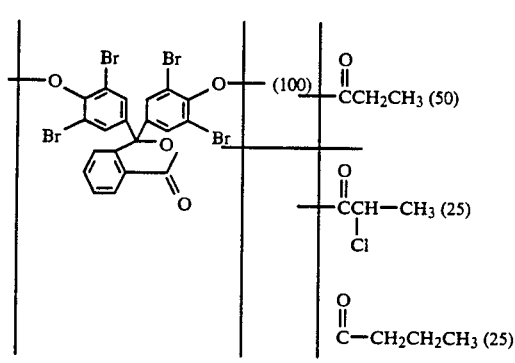
Tg = 69° C.
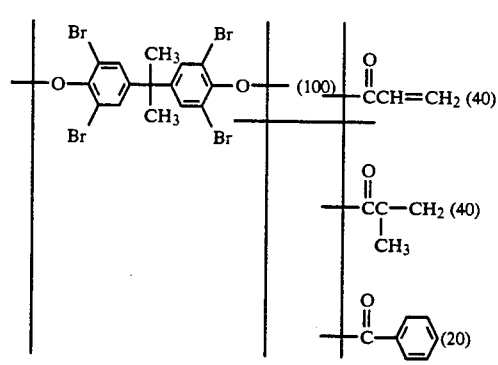
Tg = 55° C.
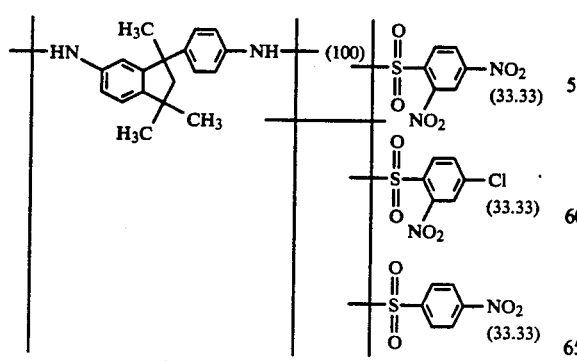
Tg = 85° C.
TABLE II-continued
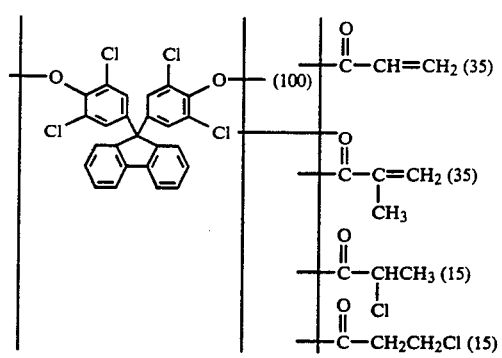
Tg = 65° C.
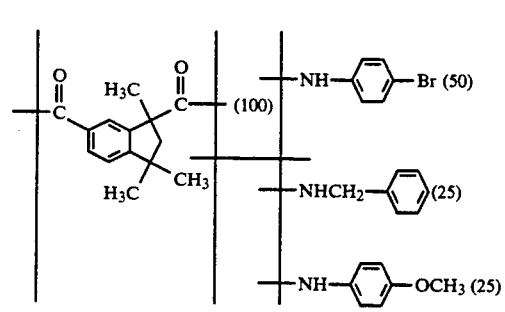
Tg = 112° C
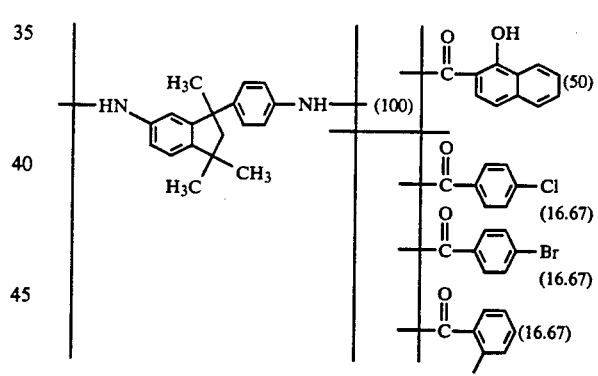
Tg = 118° C.
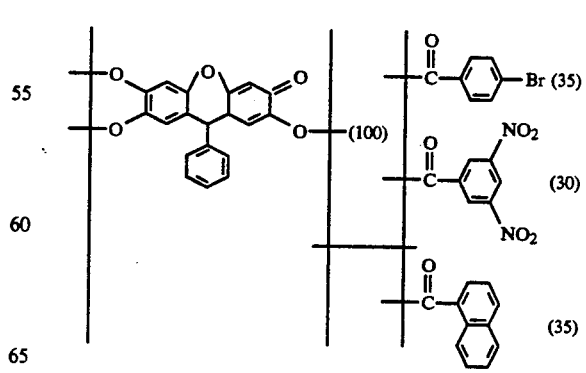
Tg = 114° C.

TABLE II-continued

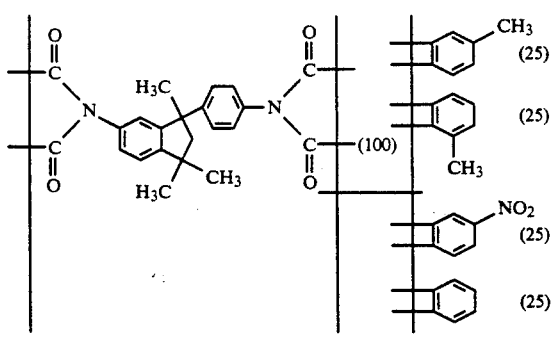

Tg = 115° C.

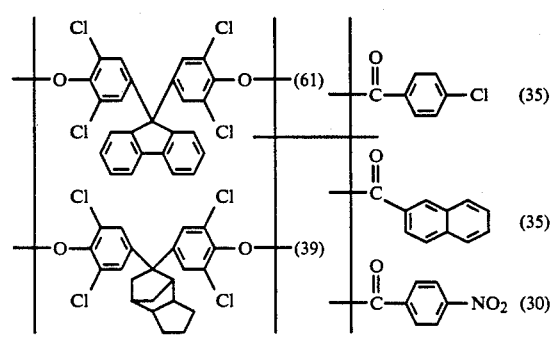

Tg = 101° C.

EXAMPLE 4

A dry toner was made using the product mixture of Example 1, monomeric glass of the following structure:

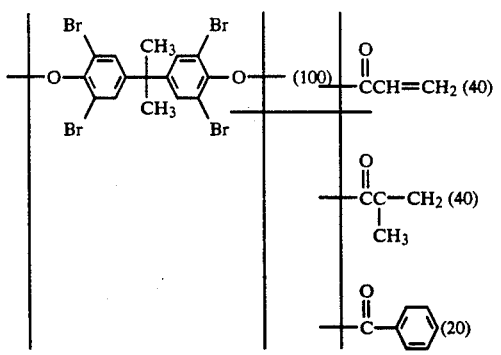

A 10% methylene chloride solution of the product mixture of Example 1, 39.8 g, was stirred together with 65.33 g of the following mill grind:

6% "Sunfast" Quinacridone pigment (a product of Sun Chemicals Co., 200 Park Avenue, New York, N.Y. 10166)

6% styrene-co-lithium methacrylate (a pigment dispersing aid)

88% methylene chloride

The methylene chloride was evaporated by exposure in a large aluminum dish, first in air for about 2 days and then in a vacuum oven for about one week. Recovered 46.8 g of solids which were ground for use as a toner. The final toner contained a ratio of "Sunfast" pigment/styrene-co-lithium methacrylate/Example 1 product mixture of 1/1/10 and exhibited a number of average particle size of 3.1 μm and a volume average size of 5.1 μm. This toner exhibited a negative polarity ($\theta$ 14.5 micro coulombs per gram) when mixed with a ferrite iron carrier. When mixed with a similar ferrite carrier which comprised a fluorocarbon coating, the toner exhibited a positive polarity ($\oplus$ 38.3 micro coulombs per gram).

The subject toners were mixed with a polyvinylidene fluoride coated carrier and the resultant developer, 5% toner concentration, used in a magnetic brush applicator to develop electrostatic charge patterns on a single use film (Kodak Ektavolt Recording Film type SO-101) and a reusable, Kodak Ektaprint photoconductor film. The images' hot-air fusability was greater than that of polymer-based toned images. It was noted that the images produced were sharp.

The examples reported here are by no means exhaustive. It is well understood that many modifications that would be obvious to those familiar with the art, can be made to optimize certain performances. It is also conceivable to use the novel nonpolymeric amorphous glasses of this invention in combination with polymeric binders. The toner compositions incorporating the binders of this invention can be negative or positive working, depending upon the structure of the binder, or the nature of the charge carriers used with binders.

Furthermore, when the binders of this invention contain polymerizable or crosslinkable groups such as acrylates, methacrylates and the like, the toner derived from them can be cured or crosslinked, either by light, electrical, or heat energy.

Even though the examples reported are for dry toner and developer compositions, it is understood that the binders of this invention can also be used in liquid developer compositions.

The reported examples of dry toners were prepared by jet mill pulverization, but the binders of this invention can also be used to prepare dry toners via other known techniques such as spray drying.

Although the invention has been described in considerable detail with particular reference to certain preferred embodiments thereof, variations and modifications can be effected within the spirit and scope of the invention.

We claim:

1. A dry developer composition for developing electrostatic images, comprising:
   (a) carrier particles, and
   (b) a powdered toner composition of finely divided thermally fusible particles, which particles comprise a homogeneous blend of:
      (1) a major amount of a nonpolymeric amorphous binder composition, and
      (2) a colorant; said binder composition comprising a homogeneous mixture of at least two nonpolymeric, thermoplastic compounds each independently conforming to the structure $$(R^1Y^1)_pZ^2Y^4R^3;$$

wherein
   p is an integer of from one to eight;
   each $R^1$ and $R^3$ is independently a monovalent aliphatic or cycloaliphatic hydrocarbon group having 1 to 20 carbon atoms, an aromatic group or a multicyclic aromatic nucleus;

$Z^2$ represents a multivalent aliphatic or cycloaliphatic hydrocarbon group having 1 to 20 carbon atoms or an aromatic group;

$Y^1$ and $Y^4$ each independently represents a linking group;

provided that at least one of $R^1$ and $Z^2$ is an aromatic group and the mixture has a glass transition temperature of 50° to 120° C.

2. The dry developer composition of claim 1, wherein $Y^1$, and $Y^4$ each independently represents an ester (—COO—), an amide (—CONH—), an urethane (—NHCOO—), an imide

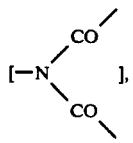

a nitrilomethyleneoxy

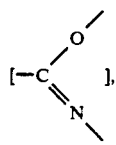

a nitrilomethyleneimino

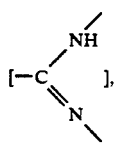

a nitrilomethylenethio

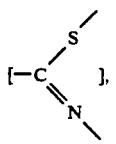

or a 1,3,4-triazol-2,5-ylene

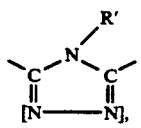

wherein R' represents alkyl of 1-6 carbon atoms, hydroxyl, amino or aryl.

3. The dry developer composition of claim 1, wherein;

p is one to eight;

$R^1$ and $R^3$ each independently represent methyl, ethyl, propyl, isopropyl, butyl, hexyl, 2-ethylhexyl, methoxyethyl, ethoxycarbonylpropyl, 3-oxobutyl, 3-thiapentyl, furfuryl, 2-thiazolylmethyl, cyclohexylmethyl, benzyl, phenethyl, phenoxyethyl, vinyl, 2-methylvinyl, pyridyl, phenyl, tolyl, xylyl, naphthyl, anthryl, triptycenyl, p-chlorophenyl, p-nitrophenyl, p-bromophenyl, 2,4-dichlorophenyl, 2-chlorophenyl, 3,5-dinitrophenyl, p-(tetrabromophthalimido)phenyl, p-(tetrachlorophthalimido)phenyl, p-(tetraphenylphthalimido)phenyl, p-naphthalimidophenyl, p-(4-nitrophthalimido)phenyl, p-phthalimidophenyl, 1-hydroxy-2-naphthyl, 3,5-dibromo-4-(4-bromobenzoyloxy)phenyl, 3,5-dibromo-4-(3,5-dinitrobenzoyloxy)phenyl or 3,5-dibromo-4-(1-naphthoyloxy)phenyl;

$Z^2$ represents a nucleus derived from 9,9-bis(4-hydroxy-3,5-dichlorophenyl)fluorene; 4,4'-hexahydro-4,7-methanoindan-5-ylidenebis(2,6-dichlorophenol); 9,9-bis(4-hydroxy-3,5-dibromophenyl)fluorene; 4,4'-hexahydro-4,7-methanoindan-5-ylidenebis(2,6-dibromophenol); 3',3'',5',5''-tetrabromophenolphthalein; 9,9-bis(4-aminophenyl)fluorene, phenylindandiol, 1,1'-spirobiindandiol; 1,1'-spirobiindaniamine, 2,2'-spirobichroman; 7,7-dimethyl-7H-dibenzoxanthenediol; xanthylium salt diols; 9,9-dimethylxanthene-3,6-bis(oxyacetic acid), 4,4'(3-phenyl-1-indanylidene)diphenol, 3',3'-dibromo-5',5''-dinitro-2',2''-oxaphenolphthalein or 9-phenyl-3-oxo-2,6,7-trihydroxyxanthene; and $Y^1$ and $Y^4$ each independently represents an ester, urethane, amide or imide linking group.

4. The dry developer composition of claim 1, wherein the mixture has a glass transition temperature of 55° to 80° C.

5. The dry developer composition of claim 1, wherein the carrier is a ferrite carrier.

6. The dry developer composition of claim 1, wherein the ferrite carrier is a strontium or a barium ferrite carrier.

7. The dry developer composition of claim 1, further comprising (c) a charge control agent.

8. A dry developer composition for developing electrostatic images, comprising:

(a) carrier particles, and (b) a powdered toner composition of finely divided thermally fusible particles, which particles comprise a homogeneous blend of:

(1) a major amount of a nonpolymeric amorphous binder composition, and (2) a colorant;

said binder composition comprising a homogeneous mixture selected from the group consisting of

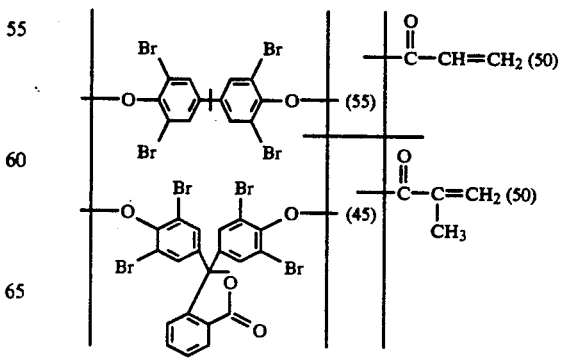

-continued
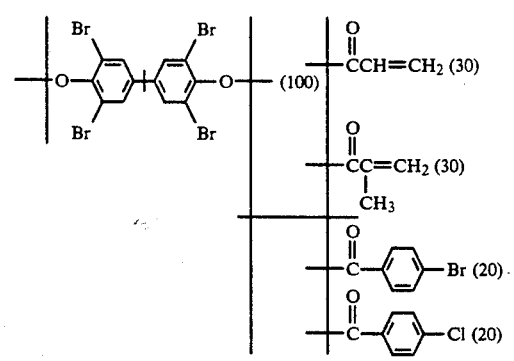
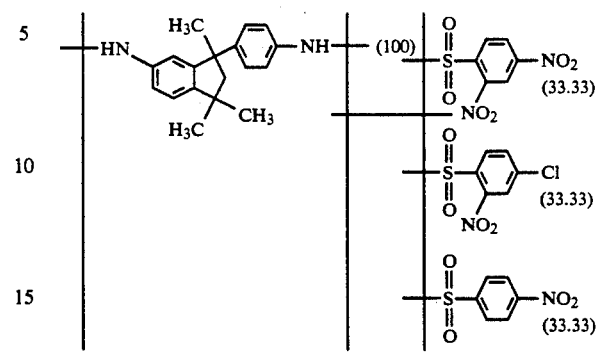
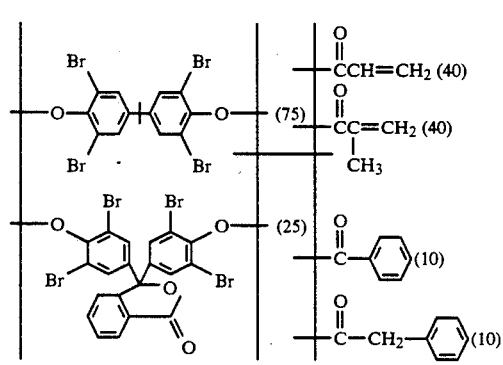
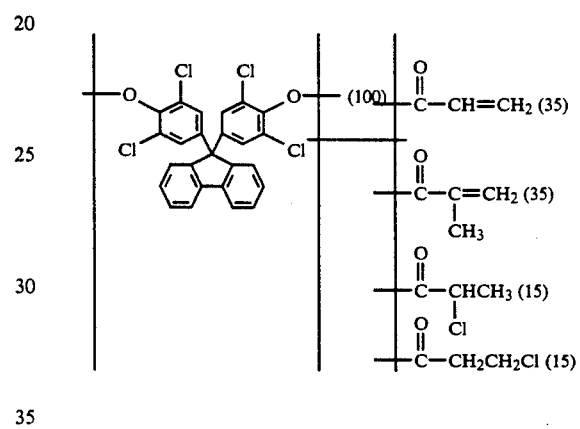
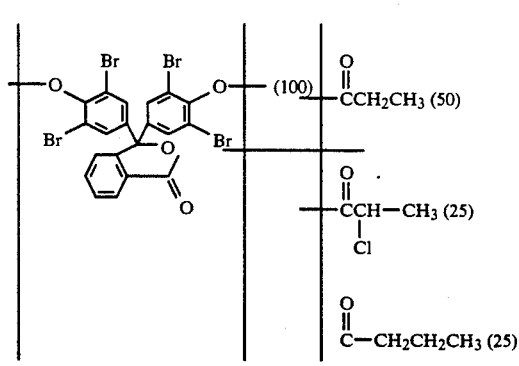
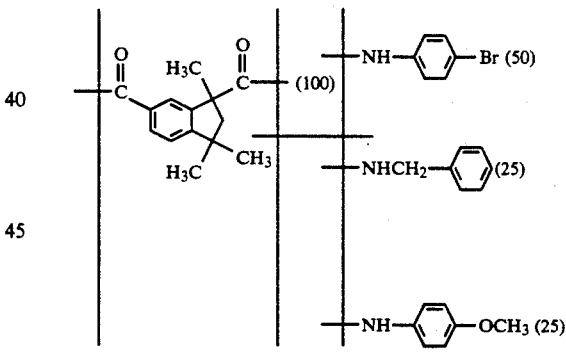
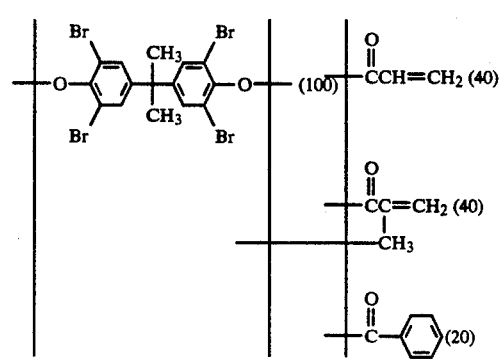
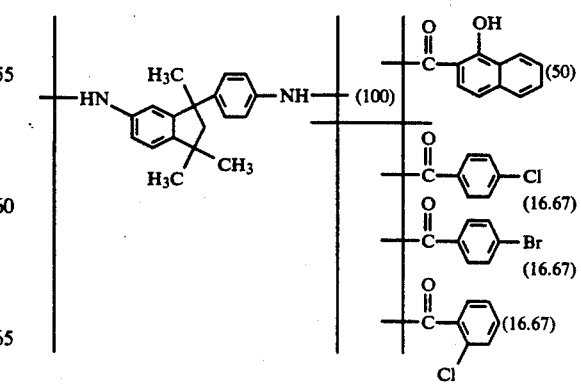

-continued

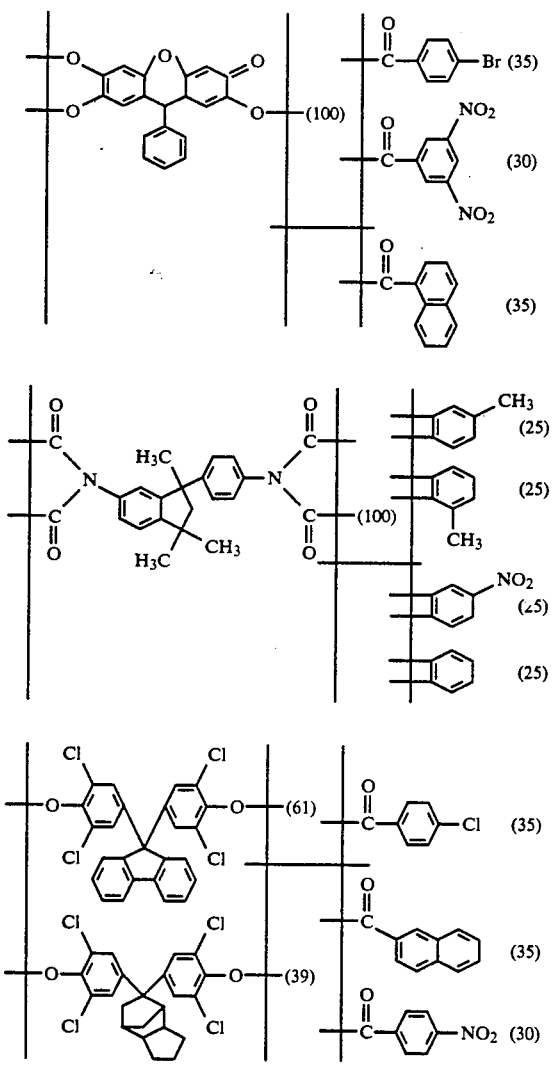

9. The dry developer composition of claim 8, wherein the carrier is a ferrite carrier.

10. The dry developer composition of claim 9, further comprising (c) a charge control agent.

11. A dry developer composition for developing electrostatic images, comprising:
(a) carrier particles, and
(b) a powdered toner of finely divided thermally fusible particles, which particles comprise a homogeneous blend of:
(1) a major amount of nonpolymeric amorphous binder composition, and
(2) a colorant;

said binder composition comprising a homogenous mixture of at least two nonpolymeric, thermoplastic compounds each independently conforming to the formula $$Z(Y-R)_n$$

wherein
n is two to eight;
Z is a straight or branched chain, substituted or unsubstituted aliphatic group optionally having hereto atom groups in or appended thereto, or a substituted or unsubstituted homo- or heterocyclic, mono- or polycyclic group;

each R group independently from the other R groups is a straight or branched chain, substituted or unsubstituted aliphatic group optionally having hetero atom groups in or appended thereto or a substituted or unsubstituted homo- or heterocyclic, mono- or polycyclic group;

each Y group, which may be the same or different from the other Y groups, is an ester, amide, imide, or urethane linkage joining the nucleus Z to a group R;

provided that at least one Z or R group is an aromatic group, the mixture comprises at least two different R groups and the mixture has a glass transition temperature of 50° to 120° C.

12. The dry developer composition of claim 11, wherein the mixture has a glass transition temperature of 55° to 80° C.

13. The dry developer composition of claim 11, wherein the carrier is a ferrite carrier.

14. The dry developer composition of claim 11, wherein the ferrite carrier is a strontium or barium ferrite carrier.

15. The dry developer composition of claim 11, further comprising (c) a charge control agent.

16. A process for developing an electrostatic latent image, comprising:
depositing a powdered toner composition of finely divided thermally fusible particles on said latent image, which particles comprise a homogeneous blend of
(a) a major amount of a nonpolymeric amorphous binder composition, and
(b) a colorant;

said binder composition comprising a homogeneous mixture of at least two nonpolymeric, thermoplastic compounds each independently conforming to the structure $$(R^1Y^1)_pZ^2Y^4R^3;$$

wherein
p is an integer of from one to eight;
each $R^1$ and $R^3$ is independently a monovalent aliphatic or cycloaliphatic hydrocarbon group having 1 to 20 carbon atoms, an aromatic group or a multicyclic aromatic nucleus;
$Z^2$ represents a multivalent aliphatic or cycloaliphatic hydrocarbon group having 1 to 20 carbon atoms or an aromatic group;
$Y^1$ and $Y^4$ each independently represents a linking group;
provided that at least one of $R^1$, $R^3$ and $Z^2$ is an aromatic group and the mixture has a glass transition temperature of 50° to 120° C.

17. The process of claim 16, wherein the mixture is selected from the group consisting of -continued
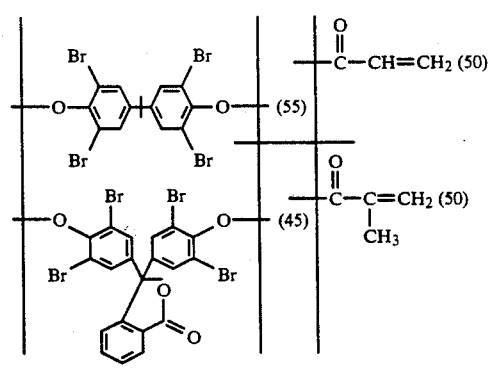
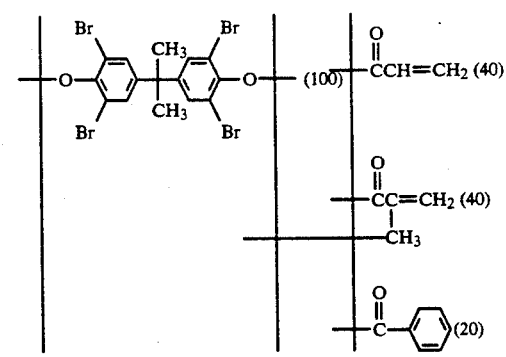
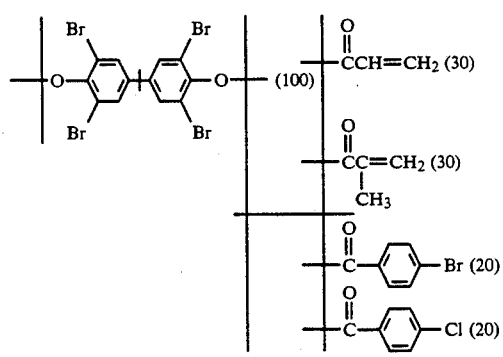
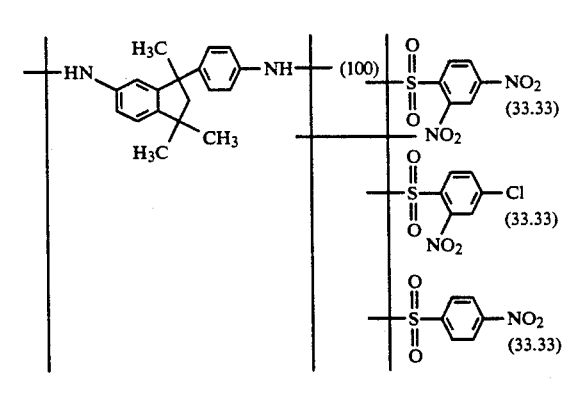
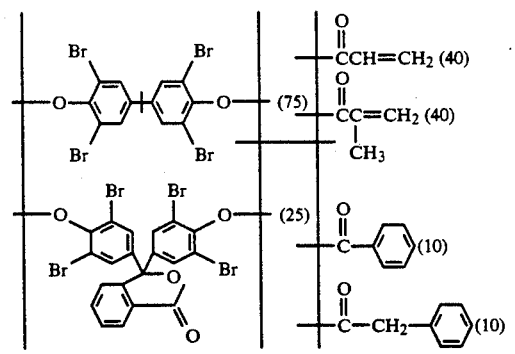
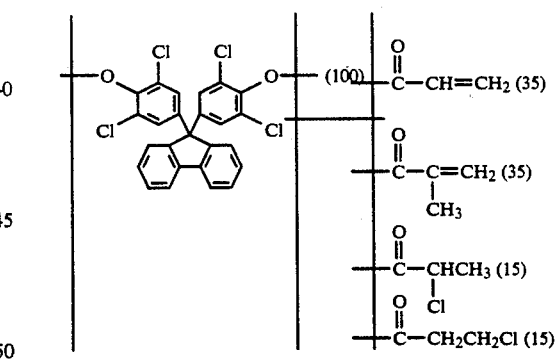
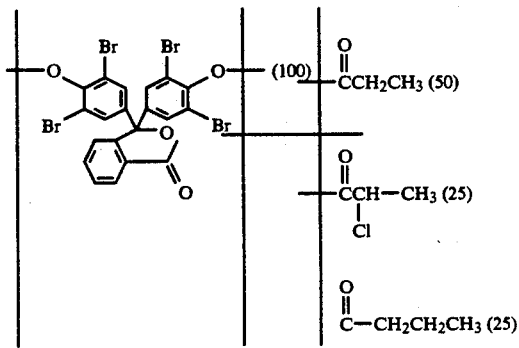
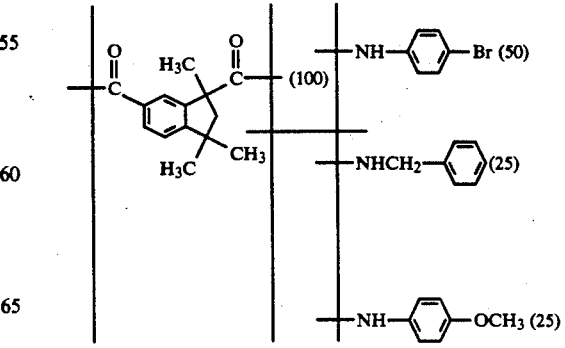

-continued

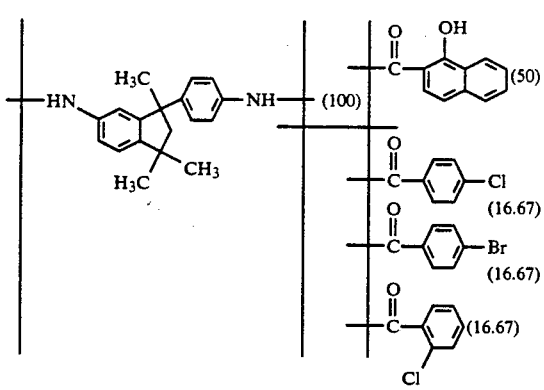

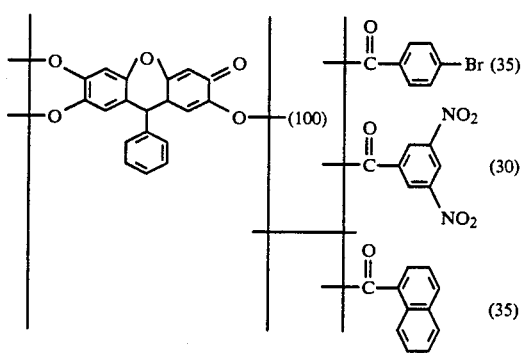

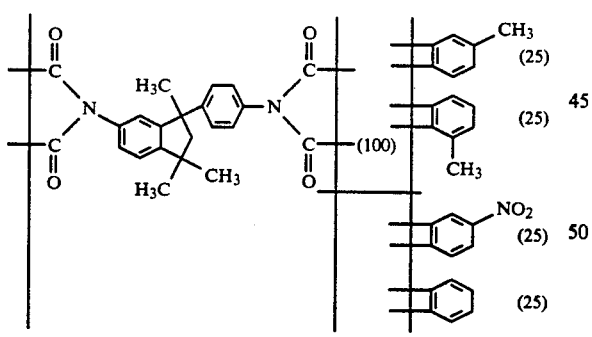

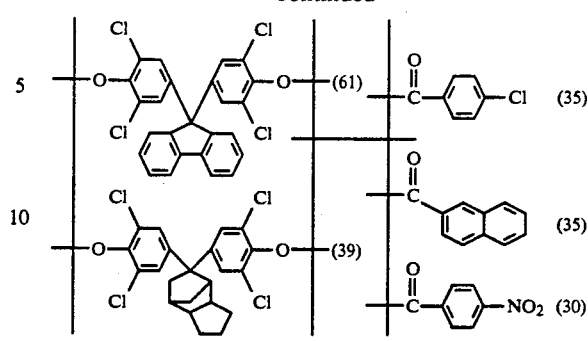

18. The process of claim 17, wherein the mixture has a glass transition temperature of 55° to 80° C.

19. The process of claim 16, wherein the mixture has a glass transition temperature of 55° to 80° C.

20. A process for developing an electrostatic latent image, comprising:
    depositing a powered toner composition of finely divided thermally fusible particles on said latent image, which particles comprise a homogeneous blend of
    (a) a major amount of a nonpolymeric amorphous binder composition, and
    (b) a colorant;
    said binder composition comprising a homogenous mixture of at least two nonpolymeric, thermoplastic compounds each independently conforming to the formula $$Z(Y-R)_n$$

wherein
    n is two to eight;
    Z is a straight or branched chain, substituted or unsubstituted aliphatic group optionally having hereto atom groups in or appended thereto, or a substituted or unsubstituted homo- or heterocyclic, mono- or polycyclic group;
    each R group independently from the other R groups is a straight or branched chain, substituted or unsubstituted aliphatic group optionally having herero atom groups in or appended thereto or a substituted or unsubstituted homo- or heterocyclic, mono- or polycyclic group;
    each Y group, which may be the same or different from the other Y groups, is an ester, amide, imide or urethane linkage joining the nucleus Z to a group R;
    provided that at least one Z or R group is an aromatic group, the mixture comprises at least two different R groups and the mixture has a glass transition temperature of 50° to 120° C.

* * * * *